(12) United States Patent
Strasser, Jr. et al.

(10) Patent No.: US 10,512,286 B2
(45) Date of Patent: Dec. 24, 2019

(54) COLORIMETRIC AEROSOL AND GAS DETECTION FOR AEROSOL DELIVERY DEVICE

(71) Applicant: RAI Strategic Holdings, Inc., Winston-Salem, NC (US)

(72) Inventors: Josef Strasser, Jr., Greensboro, NC (US); Courtney G. Culbert, Pfafftown, NC (US); David T. Szabo, Durham, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 170 days.

(21) Appl. No.: 15/788,174

(22) Filed: Oct. 19, 2017

(65) Prior Publication Data

US 2019/0120769 A1 Apr. 25, 2019

(51) Int. Cl.
| | |
|---|---|
| *A24F 47/00* | (2006.01) |
| *G01N 21/78* | (2006.01) |
| *A24C 5/34* | (2006.01) |
| *A61M 15/06* | (2006.01) |
| *G01N 31/22* | (2006.01) |

(Continued)

(52) U.S. Cl.
CPC .......... *A24F 47/008* (2013.01); *A24C 5/3406* (2013.01); *A24F 47/002* (2013.01); *A24F 47/004* (2013.01); *A61M 11/042* (2014.02); *A61M 15/0021* (2014.02); *A61M 15/06* (2013.01); *G01N 21/783* (2013.01); *G01N 31/22* (2013.01); *A61M 2205/0227* (2013.01); *A61M 2205/584* (2013.01); *A61M 2205/8206* (2013.01); *G01N 31/224* (2013.01)

(58) Field of Classification Search
CPC ..................................................... A24F 47/008
See application file for complete search history.

(56) References Cited

U.S. PATENT DOCUMENTS

| | | |
|---|---|---|
| 3,217,715 A | 11/1965 | Berger et al. |
| 3,350,175 A | 10/1967 | Gross et al. |
| 3,957,563 A | 5/1976 | Sexstone |

(Continued)

FOREIGN PATENT DOCUMENTS

| | | |
|---|---|---|
| EP | 579410 | 1/1994 |
| WO | WO 2006/064371 | 6/2006 |

(Continued)

*Primary Examiner* — James Harvey
(74) *Attorney, Agent, or Firm* — Womble Bond Dickinson (US) LLP

(57) ABSTRACT

The present disclosure relates to a colorimetric aerosol detection device for detecting target compounds in an aerosol generated from an aerosol delivery device. The colorimetric aerosol detection device includes a tubular housing with a first open end (which can be configured to engage a mouthpiece of the aerosol delivery device) and a second open end (which may be configured as a mouthpiece) such that a stream of vapor can pass through the tubular housing in a direction from the first open end to the second open end. A colorimetric indicator material is located inside the tubular housing, and is configured to signal detection of a target compound in the vapor stream by a change in color visible to the user through a transparent or translucent portion of the tubular housing.

30 Claims, 4 Drawing Sheets

(51) Int. Cl.
*A61M 11/04* (2006.01)
*A61M 15/00* (2006.01)

(56) References Cited

U.S. PATENT DOCUMENTS

| | | | |
|---|---|---|---|
| 4,174,720 A | 11/1979 | Hall | |
| 4,201,234 A | 5/1980 | Neukomm | |
| 4,223,597 A | 9/1980 | Lebert | |
| 4,771,795 A | 9/1988 | White et al. | |
| 5,027,837 A | 7/1991 | Clearman et al. | |
| 5,137,034 A | 8/1992 | Perfetti et al. | |
| 5,360,023 A | 11/1994 | Blakley et al. | |
| 5,568,819 A | 10/1996 | Gentry et al. | |
| 5,620,658 A | 4/1997 | Jaunakais | |
| 5,622,190 A | 4/1997 | Arterbery et al. | |
| 6,537,186 B1 | 3/2003 | Veluz | |
| 6,584,979 B2 | 7/2003 | Xue et al. | |
| 6,761,174 B2 | 7/2004 | Jupe et al. | |
| 6,789,547 B1 | 9/2004 | Paine, III | |
| 6,789,548 B2 | 9/2004 | Bereman | |
| 7,726,320 B2 | 6/2010 | Robinson et al. | |
| 2002/0020420 A1 | 2/2002 | Xue et al. | |
| 2002/0166563 A1 | 11/2002 | Jupe et al. | |
| 2003/0154993 A1 | 8/2003 | Paine et al. | |
| 2003/0168070 A1 | 9/2003 | Xue et al. | |
| 2003/0200973 A1 | 10/2003 | Xue et al. | |
| 2004/0194792 A1 | 10/2004 | Zhuang et al. | |
| 2004/0226569 A1 | 11/2004 | Yang et al. | |
| 2004/0237984 A1 | 12/2004 | Figlar et al. | |
| 2005/0049128 A1 | 3/2005 | Buhl et al. | |
| 2005/0066984 A1 | 3/2005 | Crooks et al. | |
| 2005/0133051 A1 | 6/2005 | Luan et al. | |
| 2006/0144410 A1 | 7/2006 | Luan et al. | |
| 2006/0180164 A1 | 8/2006 | Paine, III et al. | |
| 2007/0056600 A1 | 3/2007 | Coleman, III et al. | |
| 2013/0255702 A1 | 10/2013 | Griffith, Jr. et al. | |
| 2014/0096781 A1 | 4/2014 | Sears et al. | |
| 2015/0216232 A1 | 8/2015 | Bless et al. | |
| 2018/0140016 A1* | 5/2018 | Thorens | A24F 47/008 |
| 2019/0120769 A1* | 4/2019 | Strasser, Jr. | A24F 47/004 |

FOREIGN PATENT DOCUMENTS

| | | |
|---|---|---|
| WO | WO 2013/124377 A2 | 8/2013 |
| WO | WO 2015/121077 A1 | 8/2015 |

* cited by examiner

COLORIMETRIC AEROSOL AND GAS DETECTION FOR AEROSOL DELIVERY DEVICE

FIELD OF THE DISCLOSURE

The present disclosure relates to devices, systems, and methods for detecting select target compounds in an aerosol intended for human consumption, particularly, an aerosol formed from an aerosol precursor made or derived from tobacco or otherwise incorporating tobacco.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in U.S. Pat. No. 7,726,320 to Robinson et al., U.S. Pat. Pub. No. 2013/0255702 to Griffith Jr. et al., and U.S. Pat. Pub. Nos. 2014/0096781 to Sears et al., and 2015/0216232 to Bless et al., which are incorporated herein by reference. The composition of the vapor produced from heating the volatile material can vary and generally depends on the composition of the volatile material. For example, the composition of the volatile material may contain some ingredients which are derived from natural sources (e.g., nicotine) and often contain minor impurities. Vaporization of such impure ingredients vaporizes the minor impurities as well which then become part of the composition of the vapor. Therefore, it would be of great benefit to the consumer to have access to screening tools that are able to profile the composition of the vapor for the presence or absence of vaporized impurities thereby providing valuable information about the purity of the volatile material composition (e.g., e-liquid).

SUMMARY OF THE DISCLOSURE

The present disclosure relates to detection devices, systems, and methods for detecting select target compounds in an aerosol generated from an aerosol delivery device, particularly aerosol detection devices adapted for inhalation of aerosol by a user and which includes a mouthpiece. The aerosol delivery device comprises smoking articles, and more particularly aerosol delivery devices that can utilize electrically generated heat for the production of the aerosol (e.g., smoking articles commonly referred to as electronic cigarettes). Aerosol delivery devices, such as smoking articles, configured to heat an aerosol precursor can sometimes also vaporize minor impurities (e.g., target compounds) present in the aerosol precursor. The colorimetric aerosol detection device of the invention is able to identify the presence of such target compounds in the aerosol by showing a characteristic color change of the indicator material present in the colorimetric aerosol detection device. The colorimetric aerosol detection device of the invention is designed to reversibly attach to the mouthpiece of an aerosol delivery device, e.g., electronic cigarette, and screen the aerosol emitted from the aerosol delivery device as it passes through the colorimetric detection device (e.g., after a relatively small number of puffs (e.g., after only about 2-3 puffs)). After screening is complete the colorimetric detection device of the invention can be removed from the aerosol delivery device and disposed after the consumer has visually inspected the colorimetric detection device for a color change of the indicator material. The colorimetric detection device of the invention, therefore, provides a fast and easy analysis of an aerosol for target compounds of interest, thus allowing the user to make an informed decision whether to continue with the use of the aerosol delivery device.

One aspect of the invention relates to a colorimetric aerosol detection device adapted for engagement with an aerosol delivery device having a mouthpiece, comprising a tubular housing having a first open end and a second open end such that a stream of vapor can pass through the tubular housing in a direction from the first end to the second end, wherein the first open end is configured to engage the mouthpiece of the aerosol delivery device such that vapor produced in the aerosol delivery device is in fluid communication with the first open end, and the second open end is configured as a mouthpiece through which a user can draw the stream of vapor into the tubular housing by suction, and wherein at least a portion of the tubular housing is transparent or translucent; and a colorimetric indicator material disposed inside the tubular housing between the first end and the second end, wherein the colorimetric indicator material is configured to signal detection of a target compound in the stream of vapor passing through the tubular housing by a change in color visible to the user through the transparent or translucent portion of the tubular housing.

In some embodiments, the tubular housing is made of polypropylene, polycarbonate, glass, stainless steel, or combinations thereof. In some embodiments, the transparent or translucent portion of the tubular housing has a length that is at least 50% of the longitudinal length of the tubular housing showing the colorimetric indicator material disposed inside the housing. In some embodiments, the transparent or translucent portion of the tubular housing has a concentration scale. In some embodiments, the aerosol delivery device is an electronic cigarette.

In some embodiments, the colorimetric aerosol detection device of the invention further comprises a sealing element located at the first end inside the tubular housing upstream of the colorimetric indicator material. In some embodiments, the sealing element is made of silicon or rubber. In some embodiments, the sealing element is a gasket. In some embodiments, the sealing element is configured to form a tight seal between the aerosol detection device and an aerosol delivery device attached thereto to prevent portions of the stream of vapor produced from the aerosol delivery device to escape from the colorimetric aerosol device into the atmosphere.

In some embodiments, the colorimetric indicator material is organic, inorganic, organometallic, transition metal complexes or a combination thereof. In some embodiments, the colorimetric indicator material is present in an amount to detect a predetermined amount of a target compound. In some embodiments, the colorimetric indicator material detects a target compound comprising an electrophilic, nucleophilic, or metal-containing functional group. In some embodiments, the colorimetric indicator material is disposed on a porous support material.

In some embodiments, the porous support material is selected from the group consisting of porous particles, particle beads, fibrous materials and combinations thereof. In some embodiments, the porous support material is selected from molecular sieves, silica gels, clays, glass beads, silica glass beads, silica sands, glass fibers, plastic fibers, polymer fibers, cellulose fibers, papers, membranes, organic cottons, wools, regenerated celluloses, and combinations thereof. In some embodiments, the colorimetric indicator material inside the tubular housing occupies at least about 50% of the total inside volume of the tubular housing.

In some embodiments, the colorimetric aerosol detection device of the invention further comprises an adsorbent material disposed inside the tubular housing located downstream of the chemical indicator material. In some embodiments, the adsorbent material is selected from activated carbon, molecular sieves, clays, activated aluminas, silica gels, ion exchange resins, polyester resins, polymers, and glass fibers. In some embodiments, the adsorbent material inside the tubular housing occupies no more than about 50% of the total inside volume of the tubular housing.

Another aspect of the invention relates to a method for detecting a target compound in a stream of vapor, the method comprising configuring a colorimetric aerosol detection device of the invention to an aerosol device such that aerosol formed in the aerosol device is passed through the colorimetric aerosol detection device as a stream of vapor and one or more target compounds in the stream of vapor is detected by the colorimetric aerosol detection device. In some embodiments, the aerosol device is attached to the first open end of the tubular housing of the colorimetric aerosol detection device and a mouthpiece is attached to the second open end of the tubular housing of the colorimetric aerosol detection device. In some embodiments, the aerosol is forced through the colorimetric aerosol detection device by the consumer drawing on the mouthpiece. In some embodiments, the amount of aerosol passing though the colorimetric aerosol detection device is about 2 to about 4 puffs. In some embodiments, the aerosol passing through the colorimetric aerosol detection device is in an amount ranging from about 100 to about 200 mL volume.

In some embodiments, the indicator material undergoes a change in color from one color to a different color when a predetermined amount of the target compound(s) is detected. In some embodiments, the target compound(s) comprises an electrophilic functional group or a nucleophilic functional group. In some embodiments, the electrophilic functional group comprises a carbonyl group or olefin group. In some embodiments, the target compounds comprise 1,3-butadiene, formaldehyde, acetaldehyde, acrolein, crotonaldehyde, methyl ethyl ketone, furfural, diacetyl, acetone, 2,3-pentanedione, or combinations thereof. In some embodiments, the nucleophilic functional group comprises a carboxyl group or a hydroxy group. In some embodiments, the target compounds comprise butyric acid, cresol, propylene glycol, or combinations thereof.

BRIEF DESCRIPTION OF THE FIGURES

Figure 1:
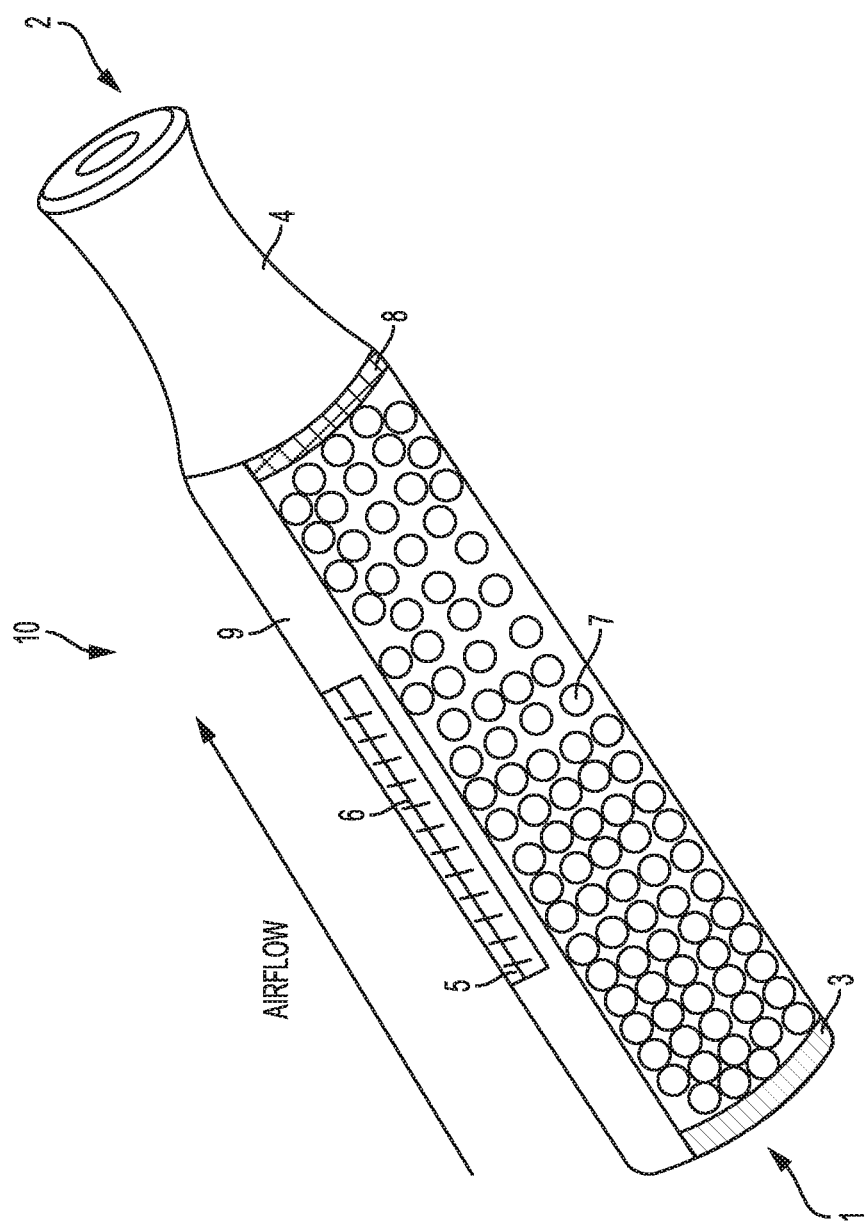
Figure 2:
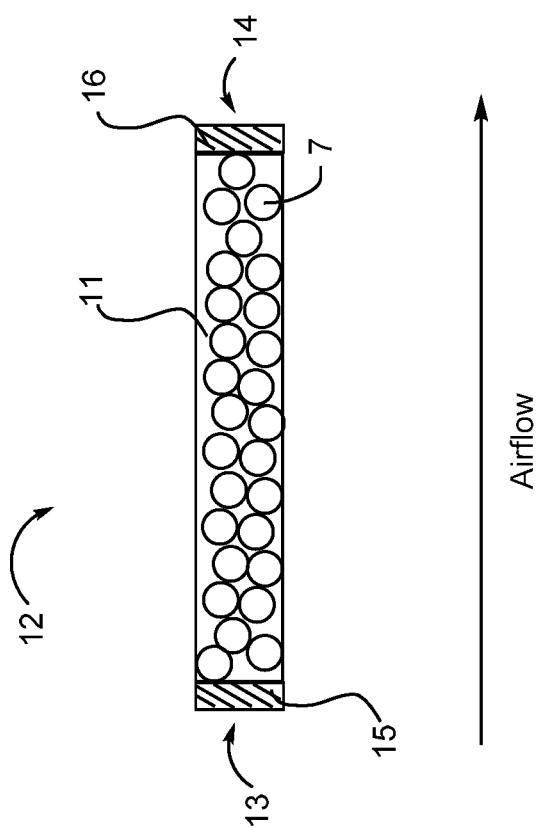
Figure 3:
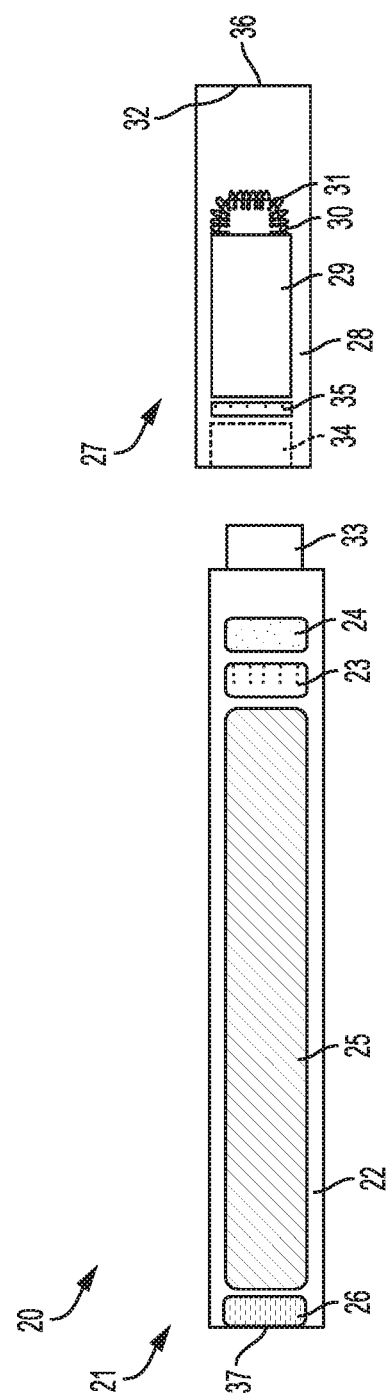
Figure 4:
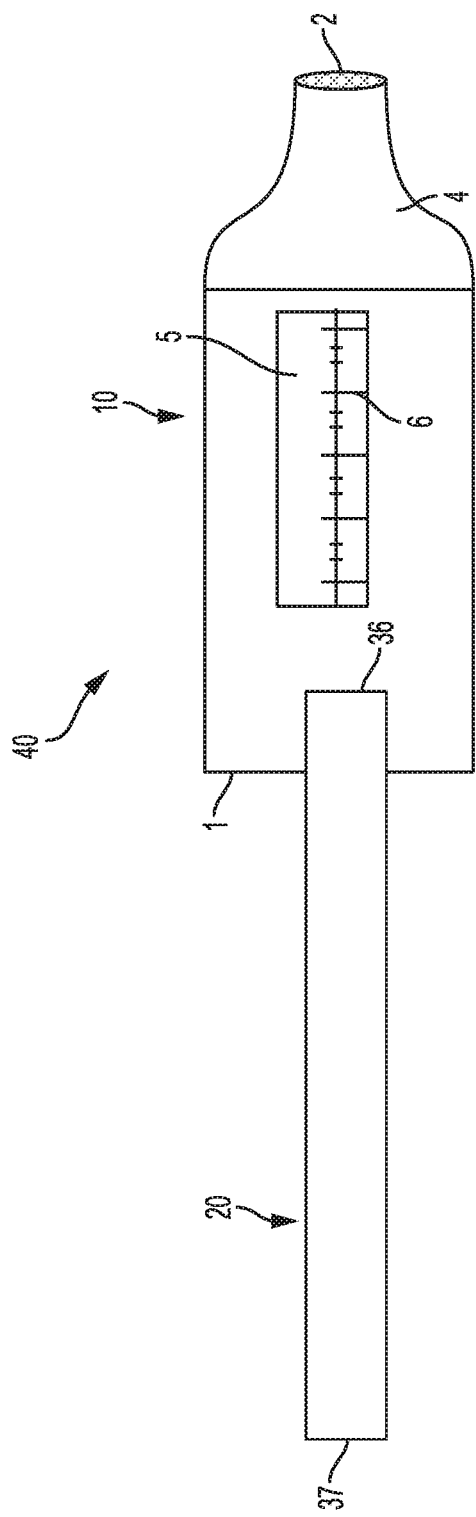

Having thus described the disclosure in the foregoing general terms, reference will now be made to the accompanying drawings, which are not necessarily drawn to scale, and wherein:

FIG. 1 is a partially cut-away view of a colorimetric aerosol detection device according to various embodiments of the present disclosure;

FIG. 2 is a cross-sectional view of an indicator tube according to embodiments of the present disclosure;

FIG. 3 is a cross-sectional view of an aerosol delivery device comprising a cartridge and a control body including a variety of elements that may be utilized in an aerosol delivery device according to embodiments of the present disclosure; and FIG. 4 is a view of an aerosol delivery device with a colorimetric aerosol detection device according to the invention attached thereto.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to a colorimetric detection device for the detection of select target compounds in an aerosol generated from an aerosol precursor in an aerosol delivery device. For example, aerosol delivery devices, such as electronic cigarettes use e-liquids as aerosol precursors to generate the aerosol. Often commercially available e-liquids contain minor impurities, which vaporize during the vaporization of the e-liquid. Detection of the presence or absence of such minor impurities in the e-liquid and/or formation of harmful and potentially harmful constituents (HPHC) from the vaporization of the e-liquid with a colorimetric detection device provides valuable information to the consumer about the chemical composition and quality (e.g., purity) of the commercially available e-liquid prior to consumption.

Typically the colorimetric aerosol detection device is reversibly attached to the aerosol delivery device (e.g., an electronic cigarette) when screening the aerosol for impurities (e.g., e-liquid impurities or HPHCs), which are often referred to as target compounds. Once attached to the aerosol delivery device, the vapor generated by the delivery device passes through the detection device, which contains a colorimetric indicator material. The material will undergo a color-changing reaction upon detection of a target compound, which can be visualized by the consumer. Once the screening of the aerosol is complete the colorimetric aerosol detection device is disposed. The colorimetric detection device and the aerosol delivery device will be described in more detail below.

Colorimetric Aerosol Detection Device

The colorimetric aerosol detection device of the present disclosure generally includes a number of components provided within an outer body or shell, which may be referred to as a housing. The overall design of the outer body or shell can vary, and the format or configuration of the outer body that can define the overall size and shape of the colorimetric aerosol detection device can vary. Typically, an elongated body can be formed from a single, unitary housing. For example, the colorimetric aerosol detection device can comprise a single elongated shell or body that can be substantially tubular in shape. The diameter and length of the tubular elongated shell or body can vary, but typically depends on the number of components located inside the tubular housing and the size of each component. In some embodiments, the outer housing or shell of the colorimetric aerosol detection device is not substantially tubular in shape but may be formed to substantially greater dimensions. For example, the single, unitary housing or shell can be further configured to include a mouthpiece.

The colorimetric aerosol detection device of the present disclosure comprises additional components, which are contained within the housing. For example, in certain embodiments, additional components comprise a sealing element (e.g., a gasket), at least one colorimetric indicator material, an adsorbent material, and an indicator tube. More specific formats, configurations and arrangements of components within the colorimetric aerosol detection device of the present disclosure will be evident in light of the further disclosure provided hereinafter.

One example embodiment of a colorimetric aerosol detection device 10 is provided in FIG. 1. A single tubular housing 9 is shown having a first open end 1 and a second open end 2. The first open end 1 is configured to engage with the mouthpiece of an aerosol delivery device and can include an optional sealing element 3 located inside the first end 1 of the tubular housing 9. The second open end 2 is configured as a mouthpiece 4, which the consumer can draw on.

The tubular housing is made from any suitable material such as, but not limited to, polypropylene, polycarbonate, glass, stainless steel, or combinations thereof. In some embodiments, the entire tubular housing is transparent or translucent. In some embodiments, only a portion of the tubular housing is transparent or translucent. A translucent or transparent portion of the tubular housing has a length ranging from about 5% to about 95%, from about 15% to about 90%, or from about 25% to about 75% of the longitudinal length of the tubular housing (e.g., at least 10%, at least 20%, at least 30%, at least 40%, at least 50%, at least 60%, at least 70%, at least 80%, or at least 90% of the longitudinal length of the tubular housing (with an upper limit of 100%)). A translucent or transparent portion of the tubular housing has a crosswise length ranging from about 5% to about 95%, from about 25% to about 90%, or from about 35% to about 75% of the crosswise length of the tubular housing (or at least 10%, at least 20%, at least 30%, at least 40%, at least 50%, at least 60%, at least 70%, at least 80%, or at least 90%, of the crosswise length of the tubular housing (with an upper limit of 100%)). In some embodiments, the colorimetric indicator material disposed inside the tubular housing is visible through the translucent or transparent portion of the housing. The translucent or transparent portion 5 of the tubular housing may also include a concentration scale 6, which can be printed or otherwise affixed within or on either side of the translucent or transparent portion 5. The units displayed by the concentration scale can vary. For example, the concentration scale can have units such as parts per million (ppm). In some embodiments, the concentration scale is visualized with printed colored ink.

The sealing element 3 can be configured to form a tight seal during use when the first open end of the colorimetric aerosol detection device is attached to a mouthpiece of the aerosol delivery device. In particular, the sealing element is designed to allow different sizes of mouthpiece of an aerosol delivery device to fit into the tubular housing forming a tight seal between the two components (i.e., the aerosol detection device and the aerosol delivery device). The sealing element can be made of any material or combination of materials known in the art to form a tight seal. For example, such materials include, but are not limited to paper, rubber, silicone, metal, cork, felt, neoprene, nitrile rubber, fiberglass, polytetrafluoroethylene (otherwise known as PTFE or Teflon), plastic polymer (such as polychlorotrifluoroethylene), or a combination thereof. In some embodiments, the sealing element is made of rubber or silicon.

The shape of the sealing element can vary and is designed to complement the three-dimensional shape of the inside housing forming a tight seal between the first end of the housing of the detection device and the mouthpiece of the aerosol delivery device. In some embodiments, the sealing element comprises a substantially circular shape having a hollow inner cross section. The shape of the hollow inner cross section of the sealing element is typically circular. For example, the shape of the hollow inner cross section of the sealing element is a circle or ellipse. The diameter of the hollow inner cross section can vary. For example, a wide diameter hollow inner cross section allows for larger amounts of aerosol generated by the aerosol delivery device to pass into the detection device than a smaller diameter hollow inner cross section. In some embodiments, the size of the diameter hollow inner cross section determines, in part, the amount of aerosol entering the colorimetric aerosol detection device. In some embodiments, the sealing element is a gasket or an o-ring.

The colorimetric aerosol detection device 10 can also include at least one or more colorimetric indicator materials 7, which are located upstream of the sealing element 3 inside the tubular housing 9. The amount of colorimetric indicator material located inside the tubular housing can vary but typically occupies about 10% to about 98%, about 20% to about 95%, about 30% to about 90%, about 40% to about 85%, about 50% to about 80% of the total inside volume of the tubular housing (or at least about 10%, at least about 20%, at least about 30%, at least about 40%, at least about 50%, at least about 60%, at least about 70%, at least about 80%, at least about 90% of the total inside volume of the tubular housing. The colorimetric indicator material, generally, comprises a material that can undergo a color-changing reaction, when exposed to vapor phase components (e.g., target compounds). In some embodiments, the colorimetric indicator material is organic or inorganic. Exemplary colorimetric indicator materials that are commercial include material sold by Sensidyne Industrial Health and Safety Instrumentation and Honeywell (e.g., RAE systems colorimetric gas detection tubes).

In some embodiments, the color-changing reaction of the colorimetric indicator material with the target compound forms a covalent bond between atoms of the colorimetric indicator material and target compound (often considered an irreversible interaction) or forms a non-covalent bond between atoms of the colorimetric indicator material and the target compound (often considered a reversible interaction). Exemplary types of colorimetric indicator materials include, but are not limited to, acid-base indicator materials (e.g., pH indicators), oxidation-reduction indicator materials, complexometric indicator materials, and reaction-based indicator materials. The amount of colorimetric indicator material can vary and typically depends on the chemical properties of the colorimetric indicator material (e.g., loading of functional groups able to detect target compound and/or reactivity of functional groups with the target compound) and/or the amount of the target compound desired to be detected (e.g., minimum amount of target compound allowable according to government agencies to detect presence by a color change of the indicator material or measuring concentrations of target compound in a given volume of aerosol).

For example, the amount of a colorimetric indicator material with a high loading of functional groups able to detect a predetermined amount of target compound will be less than the amount of a colorimetric indicator material with a lower loading of functional groups able to detect the same predetermined amount of target compound. In some embodiments, the amount of a colorimetric indicator material depends on the reactivity of the functional group able to react with a functional group of the target compound resulting in a change in color of the colorimetric indicator material. For example, the amount of a colorimetric indicator material with a highly reactive functional group towards functional groups of a target compound will be lower than the amount of a colorimetric indicator material with functional groups of lesser reactivity towards functional groups of a target compound, provided the loading of both colorimetric indicator material are the same.

In some embodiments, the amount of indicator material depends on the amount of target compound or concentration of target compound in a given aerosol volume to be detected. For example, the desired amount of target compound to be detected can be a predetermined amount (i.e., minimum amount), which when detected by the colorimetric indicator material identifies the presence or absence of the target compound (in the predetermined amount). The amount of indicator material to identify such a predetermined amount of target compound can be dependent upon, but is not limited to, the chemical properties of the indicator material mentioned above.

In some embodiments, the amount of indicator material is designed to measure the concentration of a target compound present in a predetermined volume of aerosol. For example, as a predetermined amount of aerosol passes through the bed of the colorimetric material 7 located inside the tubular housing 9 according to the airflow shown in FIG. 1, a portion of the bed containing the colorimetric indicator material changes color when detecting a target compound. In particular, the portion of the bed of indicator material changing color is located at the first open end of the colorimetric indicator device, which is visualized as a narrow colored band. As the concentration of target compound being detected in the aerosol volume increases the width of the colored band of indicator material expands because more indicator material in the bed reacts with the target compound in a concentration dependent manner. Hence, the concentration of the target compound being detected is visualized by the width of the colored band of the bed of the colorimetric indicator material having undergone a color change, which corresponds to the concentration scale 6 provided on the outside of the tubular housing 9.

In some embodiments, the colorimetric indicator material 7 is located inside an indicator tube 11 as is shown in FIG. 2, having a first open end 13 and a second open end 14. The indicator tube 11 can be made of any material that is translucent or transparent. In some embodiments, the indicator tube 11 is made of, but not limited to, polypropylene, polycarbonate, or glass. In some embodiments, the first open end 13 and/or the second open end 14 of the indicator tube 11 can optionally include a gas-permeable material 14 and/or 15, respectively, located on the inside of the indicator tube 11. The shape of the gas-permeable material 14 and/or 15 can vary and is generally designed to complement the three dimensional shape of the inside of the indicator tube 11. For example, in some embodiments, the three dimensional shape of the gas-permeable material 15 and/or 16 is in the shape of a circular pad having approximately the same dimensions as the inside diameter of the indicator tube 11.

The gas-permeable material 15 and/or 16 can be of any material or combination of materials known in the art to be gas-permeable allowing the aerosol to pass through while keeping the indicator material 7 inside the indicator tube 11. In some embodiments, only the first open end 13 includes a gas-permeable material 15. In some embodiments, only the second open end 14 includes a gas-permeable material 16. In some embodiments, the first open end 13 and the second open end 14 include gas-permeable materials 15 and 16 respectively. In some embodiments, the gas-permeable materials 15 and 16 are the same. In some embodiments, the gas-permeable materials 15 and 16 are different. In some embodiments, the gas-permeable material 15 and/or 16 is a screen or mesh material. The amount of colorimetric indicator material located inside the indicator can vary but typically occupies about 10% to about 98%, about 20% to about 95%, about 30% to about 90%, about 40% to about 85%, about 50% to about 80% of the total inside volume of the tubular housing (or at least about 10%, at least about 20%, at least about 30%, at least about 40%, at least about 50%, at least about 60%, at least about 70%, at least about 80%, at least about 90% of the total inside volume of the indicator tube. The indicator tube 12 as shown in FIG. 2 can then be inserted inside the tubular housing 9 upstream of the sealing element 3 of the aerosol detection device shown in FIG. 1. The diameter of the indicator tube 11 can vary but is typically at least about the same dimensions as the translucent or transparent portion 5 of the tubular housing 9. In some embodiments, the indicator tube comprises at least the same diameter as the crosswise length of the translucent or transparent portion 5 of the tubular housing 9. The length of the indicator tube can vary but typically is at least the same length as the translucent or transparent portion 5 of the tubular housing 9. With the indicator tube generally having smaller dimensions (e.g., diameter and/or length) than the dimensions of the tubular housing 9, a smaller amount of indicator material is generally required for aerosol detection devices employing an indicator tube, such as shown in FIG. 2, for storing the indicator material 7.

For example, in some embodiments, the amount of colorimetric indicator material can range from about 10 to about 1000 mg. In some embodiments, the colorimetric indicator material comprises an acid-base indicator material. An acid-base indicator material (e.g., pH indicator) generally includes a weekly acidic or weekly basic functional group, which can be protonated or deprotonated, respectively, by the target compound. The color-changing reaction is associated with the protonation or deprotonation of the acid-base indicator material. In some embodiments, the weekly acidic functional group of the acid-base indicator material is protonated by the target compound resulting in a color-change of the protonated acid-base indicator material. In some embodiments, the weekly basic functional group is deprotonated by the target compound resulting in a color-change of the deprotonated acid-base indicator material. In some embodiments, the acid-base indicator is selected from methyl violet, malachite green, thymol blue, methyl yellow, bromophenol blue, congo red, methyl orange, bromocresol green, methyl red, methyl purple, azolimin, bromocersol purple, bromothymol blue, phenol red, neutral red, napthol-phthalein, cresol red, cresolphthalein, thymolphthalein, alizarine yellow, indigo carmine, or combinations thereof. For additional examples of acid-base indicator materials, see, Bolts, D. F., Colorimetric Determination of Nonmetals, Volume VIII, Interscience Publishers, Inc., New York, 1958; Wolfbeis, O., Chemical Sensing Using Indicator Dyes, Optical Fiber Sensing, 1997, 4, 53-107; Mohr, G., Chromogenic and Fluorogenic Reactants: New Indicator Dyes for Monitoring Amines, Alcohols, and Aldehydes, J. Optical Sensors, 2004, 1, 51-55; Tsubaki, K., Colorimetric Recognition Using Functional Phenolphthalein Derivatives, J. Incl. Phenom. Macrocyl. Chem, 2008; and Dong-Gyu, C., Modern Reaction-Based Indicator Systems, Chem. Soc. Rev., 2009, 38, 1647-1662, which are incorporated herein by reference in their entireties.

In some embodiments, the colorimetric indicator material comprises an oxidation-reduction indicator material. An oxidation-reduction indicator material is a material that changes color due to an increase or decrease in the oxidation state. The color-changing reaction is associated with the change of the oxidation state for the material (i.e., a change in the Redox-potential of the material) in the presence of a target compound. In some embodiments, the oxidation state of the oxidation-reduction indicator material is reduced by the target compound resulting in a color-change of the reduced oxidation-reduction indicator material (i.e., reduction of the indicator material). In some embodiments, the oxidation state of the oxidation-reduction indicator material is increased by the target compound resulting in a color change (i.e., oxidation of the indicator material). In some embodiments, the oxidation-reduction indicator material is oxidized or reduced by electron transfer between the oxidation-reduction indicator material and the target compound. In some embodiments, the oxidation-reduction indicator material is oxidized or reduced due to covalent or non-covalent bond formation of the oxidation-reduction indicator material with the target compound. In some embodiments, the oxidation-reduction indicator is selected from sodium 2,6-dibromophenol-indophenol, sodium o-cresol indophenol, thionine, methylene blue, indigotetrasulfonic acid, inidgotrisulfonic acid, indigo carmine, indigomonosulfonic acid, phenosarfanin, safranin, neutral red, 2,2'-bipyridine, nitrophenantholine, N-phenylanthranilic acid, 1,10 phenanthroline iron (II) sulfate complex, N-ethoxychrysoidine, 2,2-bipyridine, 5,6-dimethylpheanthroline, o-dianisidine, sodium diphenylamine sulfonate, diphenylamine, and viologen. For additional examples on reduction/oxidation indicators, see, Tratnyek, R., Visualizing redox Chemistry; Probing Environmental Oxidation-reduction reactions with Indicator dyes, Chem. Educator, Springer Verlag New York, Inc. 2001, which is incorporated by reference herein in its entirety.

In some embodiments, the colorimetric indicator material comprises a complexomteric indicator material. A complexometric indicator material is a material that changes color in the presence of a metal ion (e.g., target compound). The color-changing reaction is associated with the complexation of the complexometric indicator material and the metal ion. Such a complexation is a non-covalent bond-forming interaction between the complexometric indicator material and the metal ion. The color-changing reaction occurs when the uncomplexed complexomteric indicator (i.e., metal-free) associates with the metal ion to form the metal-complexomteric indicator-complex (which is different in color than the metal-free complexomteric indicator). In some embodiments, the complexometric indicator material is an ionochromic dye or chelating agent. Exemplary types of complexometric indicator material include, but are not limited to, Calein, EDTA, Curcumin, Eriochrome Black T, Fast Sulphon Black, Hematoxylin, Murexide, or Xyenol Orange. For additional examples of complexometric indicator material, see, Flaschka, H., Complexometric titrations, London, Methuen, 1969, which is incorporated by reference herein in its entirety.

In some embodiments, the colorimetric indicator material comprises a reaction-based indicator material. A reaction-based indicator material is a material changing color when forming a covalent bond with a target compound to afford a reaction-based indicator-target compound adduct. The color-changing reaction is associated with the structural modification of the reaction-based indicator that occur when forming the adduct with the target compound. The formation of the covalent bond between the reaction-based indicator and target compound primarily occurs by a nucleophilic substitution reaction, although other reaction types should not be excluded. For example, in some embodiments, the reaction-based indicator material includes a nucleophilic functional group which reacts with an electrophilic functional group of the target compound to form a color-changing reaction-based indicator-target compound adduct. In some examples, the reaction-based indicator material includes an electrophilic functional group which reacts with a nucleophilic functional group of the target compound to form a color-changing reaction-based indicator-target compound adduct. Generally it is understood that the term "nucleophilic functional group" comprises functional groups with a nucleophilic center (which can be neutral or ionic in nature) as well as ionic moieties such as anions (which carry a negative charge). As such, it is also generally understood that the term "electrophilic functional group" comprises functional groups with an electrophilic center (which can be neutral or ionic in nature) as well as ionic moieties such as cations (which carry a positive charge). Examples of nucleophilic functional groups include but are not limited to basic functional group having a primary amino group (i.e., —$NH_2$), a secondary amino group (i.e., NH(alkyl group), a tertiary amino group (i.e., N(alkyl group)$_2$), a hydrazine group (—$NHNH_2$), a sulfonyl hydrazine group (—$SO_2NHNH_2$), an alcohol (—OH group), a thiol group (—SH)), or combinations thereof.

Examples of electrophilic functional groups include but are not limited to acidic functional groups such as ester groups (e.g., —COOalkyl group), carboxylic halide groups (—CO-halide), alkyl halide (—C-halide), aldehyde groups (—COH), cyanato group (—O—C≡N), isocyano groups (—N═C═O), imino group (—C═NH), oxime group (—C═NOH), sulfonyl group ($SO_2$alkyl), sulfino group (—$SO_2H$), thiocyanate group (—SCN), thioyl group (—CSalkyl), or combinations thereof.

In some embodiments, the colorimetric indicator material is disposed on a porous support. The porous support can be made of any material or combination of materials known in the art to be gas-permeable allowing for the aerosol generated by the aerosol delivery device and traveling through the colorimetric aerosol detection device to pass through. Examples of a porous support include, but are not limited to, porous particles, particle beads, foams, fibrous materials, or combinations thereof. Examples for porous particles include, but are not limited to, molecular sieves, silica gels, or clays. Examples of particle beads include, but are not limited to, glass beads, silica glass beads, or silica sands. Examples of fibrous materials, include, but are not limited to, fibers made of glass, plastic, polymers, cellulose or a cellulose derivative. Examples of fibrous materials include but are not limited to, paper (e.g., filter paper), membranes, organic cottons, wools, glass fibers, or regenerated cellulose fabrics. Examples of foams include, but are not limited to, foams made of polyurethanes, polymers, ceramics, metals, metal oxides, silicones, or combinations thereof.

The amount of aerosol passing through the porous support can be modified by the number and size of the pores (e.g., voids) present in the porous support. For example, the number of pores per inch (PPI) present in the porous support can vary, but typically ranges from about 10 to about 150 pores, about 20 to about 100 pores, about 30 to about 90 pores, or about 45 to about 80 pores per inch (PPI) (or at least about 10 pores, at least about 20 pores, at least about 30 pores, at least about 40 pores, at least about 50 pores, at least about 60 pores, at least about 70 pore, at least about 80 pores, at least about 90 pores, or at least about 100 pores per inch, with an upper boundary of about 150 pores per inch. The average diameter of the pores present in the porous support can vary and typically depends on the type of porous support. In some embodiments, the pores of the porous support comprise an average diameter ranging from about 0.001 inches to about 0.050 inches, about 0.005 inches to about 0.040 inches, about 0.010 inches to about 0.030 inches, or about 0.015 inches to about 0.020 inches (or at least about 0.050 inches, at least about 0.10 inches, at least about 0.015 inches, at least about 0.020 inches, at least about 0.030 inches, or at least about 0.040 inches, with an upper boundary of about 0.050 inches). In some embodiments, the porous support material comprises an arrestance of at least 50%, wherein the term "arrestance" is a measurement describing the ability of a porous material to remove impurities (e.g., target compounds present in the aerosol) from the air and/or aerosol. In some embodiments, the arrestance ranges from about 60% to about 98%, from about 60% to about 95%, from about 70% to about 90%, or from about 75% to about 90% (or at least 60%, at least 70%, at least 80%, at least 90%, or at least 98% with an upper boundary of 100%).

In some embodiments, the porous support comprises foams and/or fibrous materials in the form of a solid pad having a approximately the same dimensions (e.g., diameter) as the inside dimensions of the tubular housing 9 with a thickness ranging from about 0.05 to about 0.75 inches or from about 0.125 inches to about 0.5 inches.

The amount of colorimetric indicator material disposed on the porous support can vary, comprising about 1% to about 99% by weight colorimetric indicator material based on the total weight of the colorimetric indicator material-containing porous support (or at least 90% by weight colorimetric indicator material based on the total weight of the colorimetric indicator material-containing porous support with an upper boundary of 99%). For examples on the preparation of colorimetric indicator material on a support, see, U.S. Pat. No. 3,350,175 to Gross et al.; U.S. Pat. No. 3,467,601 to Brauer; and U.S. Pat. No. 5,620,658 to Jaunakais, which are incorporated by reference herein in their entireties.

In some embodiments, the colorimetric indicator material comprises a target compound-modifying agent for the chemical modification of a target compound prior to the color-changing reaction of the colorimetric indicator material. The target compound-modifying agent can be any chemical reagent suitable for modifying a target compound to render a modified target compound that can undergo a color-changing reaction with an indicator material (e.g., acid-base indicator, reduction-oxidation indicator, complexometric indicator) present in the colorimetric indicator material. Examples of target compound-modifying agents include, but are not limited to, oxidizers, reducing agents, antioxidants (e.g., hydroxyl amine), metal-containing reagents, or combinations thereof. As such, it is not the target compound that reacts with the indicator material directly but is rather first modified with a modifying agent (to form a modified target compound) before reacting with the indicator material to illicit a color change (e.g., it is the modified target compound reacting with the indicator material illiciting the color change). Examples of target compound-modifying agents frequently used include an oxidizer or hydroxyl amine.

As illustrated in FIG. 1, an adsorbent material 8 can optionally be disposed inside the tubular housing and is located downstream of the chemical indicator material before reaching the mouthpiece 4. The adsorbent material, generally, is capable of adsorbing or reacting with target compounds as the vapor passes through the device, thereby reducing the amount of target compounds present in the vapor exiting the device through the mouthpiece 4. Having a reduced amount of target compounds present in the treated vapor can provide several advantages for the consumer upon exposure of the treated vapor exiting the mouthpiece 4, such as, but not limited to, improved taste/aroma profile of the treated vapor and/or reduced exposure to target compounds.

Exemplary types of adsorbent materials include but are not limited to activated carbon, molecular sieves (e.g., zeolites and carbon molecular sieves), clays, activated aluminas, silica gels, ion exchange resins, polyester resins, polymers, and glass fibers. The amount of adsorbent materials can vary, but is typically between about 10 to about 250 mg, often about 30 to about 150 mg, and frequently about 40 to about 120 mg. The form of the adsorbent material may vary. Typically, the adsorbent material is used in granular or particulate solid form having a particle size of between about 8×16 mesh to about 30×70 mesh using the U.S. sieve system. However, smaller or larger particles could be used without departing from the invention. In some embodiments, the adsorbent material may have a particle size such that at least about 80% of the particles are from 20 to 50 mesh. The terms "granular" and "particulate" are intended to encompass both non-spherical shaped particles and spherical particles, such as so-called "beaded carbon" described in International Patent Application Publication No. WO 03/059096 to Paine, which is incorporated by reference herein.

In some embodiments, the adsorbent material may be activated carbon. Activated carbon is particularly effective in the adsorption of organic and inorganic pollutants due to the high capacity of organic molecules that bind to carbon. Activated carbon is known to be used in smoke filtration and thus it may be included as an adsorbent in the detection device to remove one or more gas phase components present in the vapor.

Activated carbon can be derived from synthetic or natural sources. Materials such as rayon or nylon can be carbonized, followed by treatment with oxygen to provide activated carbonaceous materials. Materials such as wood or coconut shells can be carbonized, followed by treatment with oxygen to provide activated carbonaceous materials. The level of activity of the carbon may vary. Typically, the carbon has an activity of about 60 to about 150 Carbon Tetrachloride Activity (i.e., weight percent pickup of carbon tetrachloride). Preferred carbonaceous materials are provided by carbonizing or pyrolyzing bituminous coal, tobacco material, softwood pulp, hardwood pulp, coconut shells, almond shells, grape seeds, walnut shells, macadamia shells, kapok fibers, cotton fibers, cotton linters, and the like. Examples of suitable carbonaceous materials are activated coconut hull based carbons available from Calgon Corp. as PCB and GRC-11 or from PICA as G277, coal-based carbons available from Calgon Corp. as S-Sorb, Sorbite, BPL, CRC-11F, FCA and SGL, wood-based carbons available from Westvaco as WV-B, SA-20 and BSA-20, carbonaceous materials available from Calgon Corp. as HMC, ASC/GR-1 and SC II, Witco Carbon No. 637, AMBERSORB 572 or AMBERSORB 563 resins available from Rohm and Haas, and various activated carbon materials available from Prominent Systems, Inc. See, also, for example, Activated Carbon Compendium, Marsh (Ed.) (2001), which is incorporated herein by reference.

Exemplary activated carbon materials have surface areas of more than about 200 $m^2/g$, often more than about 1000 $m^2/g$, and frequently more than about 1500 $m^2/g$, as determined using the Brunaver, Emmet and Teller (BET) method described in J. Amer. Chem. Soc., Vol. 60(2), pp. 309-319 (1938). Suitable examples of such carbonaceous materials are disclosed, for example, in EP 913100 to Jung et al.; WO 2008/043982 to Tennison et al.; WO 2007/104908 to White et al.; WO 2006/103404 to Cashmore et al.; and WO 2005/023026 to Branton et al.; and U.S. Pat. No. 7,370,657 to Zhuang et al., which are incorporated by reference herein. Certain carbonaceous materials can be impregnated with substances, such as transition metals (e.g., silver, gold, copper, platinum, palladium), potassium bicarbonate, tobacco extracts, polyethyleneimine, manganese dioxide, eugenol, and 4-ketononanoic acid.

In some embodiments, the adsorbent material is an ion exchange resin. Exemplary ion exchange resins comprise a polymer backbone, such as styrene-divinylbenzene (DVB) copolymers, acrylates, methacrylates, phenol formaldehyde condensates, and epichlorohydrin amine condensates, and a plurality of electrically charged functional groups attached to the polymer backbone, and can be a weak base anion exchange resin or a strong base anion exchange resin. Commercially available embodiments of such resins include DIAION® ion-exchange resins available from Mitsubishi Chemical Corp. (e.g., WA30 and DCA 11), DUOLITE® ion exchange resins available from Rohm and Haas (e.g., DUOLITE® A7), and XORBEX resins available from Dalian Trico Chemical Co. of China. See also the various adsorbent materials set forth in U.S. Pat. No. 6,779,529 to Figlar et al., which is incorporated by reference herein.

In some embodiments, the adsorbent material is a zeolite. Various zeolite types are described, for example, in U.S. Pat. No. 2,882,243 to Milton (zeolite A), U.S. Pat. No. 2,882,244 to Milton (zeolite X), U.S. Pat. No. 3,055,654 to Boley (zeolite K-G), U.S. Pat. No. 3,130,007 to Breck (zeolite Y). U.S. Pat. No. 3,247,195 to Kerr (zeolite ZK-5). U.S. Pat. No. 3,308,069 to Wadlinger (zeolite Beta), and U.S. Pat. No. 3,702,886 to Argauer (zeolite ZSM-5), which are incorporated by reference in their entireties. A source of natural zeolite in North America is the St. Cloud Mining Company. Truth or Consequences, N. Mex. Preferred zeolite materials include ZSM-5. Y-type zeolite and clinoptilolite.

In some embodiments, the adsorbent material is a polymer (e.g., polymer matt) or glass fiber-based adsorbent material. See, for example, U.S. Pat. No. 9,265,283 to Karlsson and Chinese Pat. Appl. Nos. CN103720051 to Zhaofeng and CN103949136 to Zhaofeng.

In some embodiments, a particulate adsorbent material is supported on a porous filter element. The porous filter element can be made of any material or combination of materials known in the art to be gas-permeable allowing for the aerosol generated by the aerosol device and traveling thought the detection device to pass through. Examples of porous filter elements include but are not limited to cellulose-containing material comprising one or more of cellulose acetate, cellulose triacetate, cellulose propionate, cellulose acetate propionate, cellulose acetate butyrate, nitrocellulose, cellulose sulfate, methyl cellulose, ethyl cellulose, hydroxyethyl cellulose, hydroxypropyl cellulose, hydroxyethylmethyl cellulose, hydroxypropylmethyl cellulose, ethylhydroxyethyl cellulose, carboxymethyl cellulose, and regenerated cellulose fibers. In some embodiments, the cellulose-containing material is cellulose acetate. In some embodiments, the porous filter element comprises fibers including a plurality of individual fibers (e.g., cellulose acetate fibers), wherein each individual fiber comprises a plurality of adsorbent material particles. In some embodiments, the adsorbent material is imbedded into the fiber construction of the porous filter element, meaning the adsorbent particles are dispersed within the individual filament structure, but with some portion of the particles exposed on the surface of the fiber so that the particles can interact with the aerosol. The adsorbent particles are introduced into the fiber material by mixing the particles with the fiber composition prior to fiber extrusion.

For example, adsorbent materials such as charcoals and activated carbon materials have been incorporated into a porous filter element, and manners and methods for incorporating carbonaceous materials into porous filter elements, are set forth in U.S. Pat. No. 3,217,715 to Berger et al.; U.S. Pat. No. 3,648,711 to Berger et al.; U.S. Pat. No. 3,957,563 to Sexstone; U.S. Pat. No. 4,174,720 to Hall; U.S. Pat. No. 4,201,234 to Neukomm; U.S. Pat. No. 4,223,597 to Lebert; U.S. Pat. No. 4,771,795 to White et al.; U.S. Pat. No. 5,027,837 to Clearman et al.; U.S. Pat. No. 5,137,034 to Perfetti et al.; U.S. Pat. No. 5,360,023 to Blakley et al.; U.S. Pat. No. 5,568,819 to Gentry et al.; U.S. Pat. No. 5,622,190 to Arterbery et al.; U.S. Pat. No. 6,537,186 to Veluz; U.S. Pat. No. 6,584,979 to Xue et al.; U.S. Pat. No. 6,761,174 to Jupe et al.; U.S. Pat. No. 6,789,547 to Paine III; and U.S. Pat. No. 6,789,548 to Bereman; US Pat. Appl. Pub. Nos. 2002/0166563 to Jupe et al.; 2002/0020420 to Xue et al.; 2003/0200973 to Xue et al.; 2003/0154993 to Paine et al.; 2003/0168070 to Xue et al.; 2004/0194792 to Zhuang et al.; 2004/0226569 to Yang et al.; 2004/0237984 to Figlar et al.; 2005/0133051 to Luan et al.; 2005/0049128 to Buhl et al.; 2005/0066984 to Crooks et al.; 2006/0144410 to Luan et al.; 2006/0180164 to Paine, III et al.; and 2007/0056600 to Coleman, III et al.; European Pat. Appl. 579410 to White; and PCT WO 2006/064371 to Banerjea et al.; which are incorporated herein by reference.

Aerosol Delivery System

As mentioned above the colorimetric aerosol detection device of the invention can be used to screen the aerosol generated from an aerosol delivery device for target compounds. The aerosol delivery device comprises smoking articles, and more particularly aerosol delivery devices that can utilize electrically generated heat for the production of the aerosol. As such, the colorimetric aerosol detection device can be used with a number of different aerosol delivery devices. For example, representative products of aerosol delivery devices include, but are not limited to, products that resemble many of the attributes of traditional types of cigarettes, cigars or pipes that have been marketed as ACCORD® by Philip Morris Incorporated; ALPHA™, JOYE 510™ and M4™ by InnoVapor LLC; CIRRUS™ and FLING™ by White Cloud Cigarettes; COHITA™, COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; GREEN SMOKE® by Green Smoke Inc. USA; GREENARETTE™ by Greenarette LLC; HALLIGAN™, HENDU™, JET™, MAXXQ™ PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC and VUSE® by R. J. Reynolds Vapor Company. Electrically powered aerosol delivery devices, and in particular those devices that have been characterized as so-called electronic cigarettes, e.g., devices that have been marketed under the tradenames BLU™; COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP® and SOUTH BEACH SMOKE™ are also included.

One example embodiment of a typical aerosol delivery device, i.e., electronic cigarette, 20 is provided in FIG. 3. An electronic cigarette 20 includes a first end 36, which is the mouthpiece for the consumer to draw on, and a second end 37, which includes an LED 26. As illustrated therein, a control body 21 can be formed of a control body shell 22 that can include a control component 23, a flow sensor 24, a battery 25, and an LED 26. A cartridge 27 can be formed of a cartridge shell 28 enclosing the reservoir housing 29 that is in fluid communication with a liquid transport element 30 adapted to wick or otherwise transport an aerosol precursor composition stored in the reservoir housing to a heater 31. An opening 32 may be present in the cartridge shell 28 to allow for egress of formed aerosol from the cartridge 27. Such components are representative of the components that may be present in a cartridge and are not intended to limit the scope of cartridge components that are encompassed by the present disclosure. The cartridge 27 may be adapted to engage the control body 21 through a press-fit engagement between the control body projection 33 and the cartridge receptacle 34. Such engagement can facilitate a stable connection between the control body 27 and the cartridge 21 as well as establish an electrical connection between the battery 25 and control component 23 in the control body and the heater 30 in the cartridge. The cartridge 27 also may include one or more electronic components 35, which may include an IC, a memory component, a sensor, or the like. The electronic component 35 may be adapted to communicate with the control component 23. For examples of additional aerosol delivery devices see. U.S. Patent Application Publication No. 2015/0144145 to Chang; and U.S. Pat. No. 8,881,737 to Collett, which are hereby incorporated by reference in their entireties.

The colorimetric aerosol detection device of the invention can also be used with aerosol delivery devices referred to as "heat not burn" devices where tobacco or tobacco-derived materials are heated to produce an aerosol without combusting the tobacco material. For example, certain types of cigarettes that employ carbonaceous fuel elements as a source of heat have been commercially marketed under the brand names "Premier," "Eclipse" and "Revo" by R. J. Reynolds Tobacco Company. See, for example, those types of cigarettes described in Chemical and Biological Studies on New Cigarette Prototypes that Heat Instead of Burn Tobacco, R. J. Reynolds Tobacco Company Monograph (1988) and Inhalation Toxicology, 12:5, p. 1-58 (2000). Additionally, a similar type of cigarette recently has been marketed in Japan by Japan Tobacco Inc. under the brand name "Steam Hot One." Furthermore, various types of smoking products incorporating carbonaceous fuel elements for heat generation and aerosol formation recently have been set forth in the patent literature. See, for example, the types of smoking products proposed in U.S. Pat. No. 7,836,897 to Borschke et al.; U.S. Pat. No. 8,469,035 to Banerjee et al. and U.S. Pat. No. 8,464,726 to Sebastian et al.; US Pat. Pub. Nos. 2012/0042885 to Stone et al.; 2013/0019888 to Tsuruizumi et al; 2013/0133675 to Shinozaki et al. and 2013/0146075 to Poget et al.; PCT WO Nos. 2012/0164077 to Gladden et al.; 2013/098380 to Raether et al.; 2013/098405 to Zuber et al.; 2013/098410 to Zuber et al.; 2013/104914 to Woodcock; 2013/120849 to Roudier et al.; 2013/120854 to Mironov; EP 1808087 to Baba et al. and EP 2550879 to Tsuruizumi et al.; which are incorporated by reference herein in their entirety. A historical perspective of technology related to various types of smoking products incorporating carbonaceous fuel elements for heat generation and aerosol formation may be found, for example, in the Background of US Pat. Pub. No. 2007/0215167 to Llewellyn Crooks et al., which is also incorporated herein by reference.

Method of Using a Colorimetric Aerosol Detection Device

A colorimetric aerosol detection device of the invention is attached to an aerosol delivery device in order to test the aerosol generated by the aerosol delivery device for the presence or absence of a target compound. In some embodiment, the aerosol delivery device is an electronic cigarette. FIG. 4 shows an embodiment of a configuration with an electronic cigarette 20 (or other aerosol generating devices) attached to a tubular housing of a colorimetric aerosol detection device 10. The mouthpiece 36 of the electronic cigarette 20 can be positioned in a sliceable engaging manner with a first end 1 of the colorimetric aerosol detection device 10 that can be detachably aligned in a functioning relationship. For example, the engagement of the mouthpiece 36 with the first end 1 of the electronic cigarette can be press fit, threaded, interference fit, magnetic or the like. A sealing element (not shown) may be used to promote the formation of a tight seal between the first open end 1 of the colorimetric aerosol detection device and the mouthpiece 36 of the aerosol delivery device 20 to prevent portions of the stream of aerosol produced from the aerosol delivery device 20 to escape from the colorimetric aerosol detection device 10 into the atmosphere. While the first end 1 engages with the mouthpiece 36 of the aerosol delivery device the second open end 2 provides an egress for the aerosol generated from the aerosol delivery device 20 and passed through the detection device 10, to exit the two-component system 40. The second open end 2 of the detection device 10 is configured to attach a mouthpiece 4, which the consumer can draw on during use.

When in use, a user draws on the mouthpiece 4 of the system 40 shown in FIG. 4 to allow for a stream of aerosol generated in the aerosol delivery device to travel through the tubular housing (not shown) of the aerosol detection device 10 in a direction from the first end 1 to the second end 2 where it exists. As the stream of aerosol passes through the tubular housing containing the colorimetric indicator material, target compounds in the vapor are exposed to the colorimetric indicator material. Detection of the target compound by the colorimetric indicator material is visualized with the colorimetric indicator material undergoing a color-changing reaction with the target compound. The change in color of the colorimetric indicator material is visible to the user through the transparent or translucent portion of the tubular housing 5 of the colorimetric detection device 10. In some embodiments, one or more target compounds in the stream of aerosol are detected by the colorimetric aerosol detection device 10.

The volume of aerosol passing though the colorimetric aerosol detection device can vary and typically depends on the type of aerosol delivery device being used. In some embodiments the volume of aerosol passing through the colorimetric aerosol detection device ranges from about 1 to about 6 puffs or from about 2 to about 4 puffs. In some embodiments, the aerosol passing through the colorimetric aerosol detection device is in a volume ranging from about 55 to about 330 mL volume or from about 100 mL to about 300 mL. In some embodiments, the mass of vapor produced from an aerosol delivery devices can vary and typically depends on the type of aerosol delivery device being used.

The target compound present in the aerosol can be any chemical composition of interest to a consumer for testing the presence or absence thereof in an aerosol generated from an aerosol precursor in an aerosol delivery device (e.g., electronic cigarette). Typically, the target compound in the aerosol is derived from the vaporization of minor impurities present in the aerosol precursor or components of the aerosol precursor (e.g., e-liquid). The presence of such minor impurities in the aerosol precursor can due to various reasons such as, but not limited to, impure ingredients used for the formulation of the aerosol precursor or prolonged shelf life of the aerosol precursor. As mentioned previously, most ingredients used in the formulation of the aerosol precursor contain minor impurities, which can vaporize and become part of the aerosol composition as the aerosol precursor is vaporized to afford the aerosol. In some embodiments, impurities in the aerosol precursor may form because a portion of the ingredients in the aerosol precursor have decomposed over time. Another reason may be that the stabilizing agents in the aerosol precursor, such as glycerin and propylene glycol, can undergo pyrolysis when the aerosol precursor is heated to form the aerosol. Pyrolysis of glycerin and propylene glycol are temperature-related and result in the formation of formaldehyde, acetaldehdye and acrolein, which all can be detected with the colorimetric aerosol detection device. Another reason may be that components, for example flavoring agents, in the aerosol precursor, such as diacetyl and acetyl propionyl, can vaporize and their presence can be detected with the colorimetric aerosol detection device.

Many of the target compounds present in the aerosol generated from the aerosol delivery device (e.g., electronic cigarette) and/or traditional smoking article (tobacco-based cigarette) are known. For a general listing of target compounds, see, Talbout, R., Hazardous Compounds of Tobacco Smoke, Int. J. Environ. Res. Public Health, 2011, 8, 613-628 and Long, G, Comparison of Select Analytes in exhaled Aerosol from E-cigarettes with Exhaled Smoke from Conventional Cigarette and Exhaled Breaths, Int. J. Environ. Res. Public Health, 2014, 11, 11177-11191, which are hereby incorporated by reference in their entireties. In some embodiments, target compounds referred to as "Hoffmann Analytes" are of particular interest. D. Hoffmann of the American Health Foundation recognized 44 different analytes that may be present in mainstream smoke of tobacco-containing smoking articles. Examples of Hoffmann analytes are ammonia, aminonapthalenes, benzopyrene, formaldehyde, acetaldehyde, acetone, methyl ethyl ketone, butyraldehyde, hydrogen cyanide, nitrous oxides, tobacco-specific nitrosamines (TSNAs), pyridine, quinoline, hydroquinone, phenol, cresols, tar, nicotine, carbon monoxide, 1,3-butadiene, isoprene, acrylonitrile, benzene, toluene, styrene, and others. For a complete listing of Hoffmann analytes, see, Intorp, M., Determination of the "Hoffmann Analytes" in cigarette Mainstream smoke. The Coresta 2006 Joint experiment, Contribution to Tobacco Research, 2009, 23, 4, 160-202, which is hereby incorporated by reference in its entirety. Another group of target compounds of particular interest are impurities present in tobacco-based ingredients used in the formulation of the aerosol precursor. For example, TSNAs, Cotinine, Myosmine, Nicotine-N'-Oxides, Anabasine, Nornicotine, Anatabine, β-Nicotyrine, or a combination thereof, which are in part listed under the Hoffmann analytes. The amount of impurities due to tobacco-based ingredients in the aerosol precursor can vary and depends on the amount of tobacco-based ingredients present in the aerosol precursor and/or the purity of the tobacco-based ingredients present in the aerosol precursor. For more examples on tobacco-based impurities present in aerosol, see, Trehy, M. L. et al. Analysis of Electronic Cigarette Cartridges, Refill Solutions, and smoke for Nicotine and Nicotine Related Impurities, J. Liq. Chromatogr. Relat. Technol. 34 (14), 2011, 1442-1459; and Flora J. W. et al. Nicotine-related impurities in e-cigarette cartridges and refill e-liquids, J. Liq. Chromatogr. Relat. Technol. 39 (18), 2016, 821-829.

Typically, a consumer is interested in screening the aerosol for one or more target compounds or a class of target compounds (e.g., multiple compounds containing the same functional group such as a group of aldehydes, amines, acids, ketones, etc.). The chemical properties (e.g., oxidation/reduction ability, pKa value) and structural properties (e.g., presence of absence of nucleophilic/electrophilic functional groups) of the target compound of interest to the consumer typically guides the selection of the corresponding colorimetric aerosol detection device used in screening the aerosol for the target compound of interest. For example, target compounds with a good oxidation/reduction activity can be detected with a colorimetric aerosol detection device comprising an oxidation-reduction indicator material. For example, target compounds with a high or low pKa value can be detected with a colorimetric detection device comprising an acid-base indicator material. For example, target compounds that are metal ions may be detected with a colorimetric detection device comprising a complexometric indicator material. For example, target compounds that contain functional groups reactive towards nucleophilic substitution reactions can be detected with a colorimetric detection device comprising a reaction-based indicator material.

In some embodiments, target compounds of particular interest to the consumer can be further classified to comprise nucleophilic functional groups, electrophilic functional groups, metals, or a combination thereof. In some embodiments, the target compound comprises a nucleophilic functional group such as a carboxyl group or a hydroxy group. For example, a target compound with a carboxyl group or a hydroxy group comprises butyric acid, cresol, propylene glycol, or combinations thereof. In some embodiments, a target compound comprises an electrophilic functional group such as a carbonyl group or olefin group. For example, a target compound with a carbonyl group or olefin group comprises 1,3-butadiene, formaldehyde, acetaldehyde, acrolein, crotonaldehyde, methyl ethyl ketone, furfural, diacetyl, acetoine, 2,3-pentanedione, or combinations thereof. Accordingly, as mentioned above the proper colorimetric indicator material is selected by the consumer to screen the aerosol for the absence or presence for the above listed target compounds containing either nucleophilic or electrophilic functional groups. See table 1 for examples of target compounds and methods of detection.

TABLE 1

| Target Compound | Reaction with colorimetric indicator material/target compound-modifying agents | Detection of (modified) target compounds |
|---|---|---|
| 1,3-Butadiene | $CH_2=CHCH=CH_2 + KMNO_2 \rightarrow$ Oxidation Products $CH_2=CHCH=CH_2 + Cr^{6+} + H_2SO_4 \rightarrow Cr^{3+}$ | Detection of Oxidation Products |
| Formaldehyde | $HCHO + (NH_2OH)_3 \cdot H_3PO_4 \rightarrow H_3PO_4 + HCH=NOH + H_2O$ | Liberation of $H_3PO_4$ detected by pH indicator |
| Acetaldehyde | $CH_3CHO + NH_2OH \cdot HCl \rightarrow HCl + CH_3CH=NOH + H_2O$ | Liberation of HCl detected by pH indicator |
| Acrolein | $CH_2=CHCHO + NH_2OH \cdot HCl \rightarrow HCl + CH_2CHCH=NOH + H_2O$ | Liberation of HCl detected by pH indicator |
| Butyric Acid | $CH_3CH_2CH_2COOH + NaOH \rightarrow C_3H_7COONa + H_2O$ | Liberation of conjugate base detected by pH indicator |
| Cresol | $CH_3C_6H_4OH + Cr^{4+} \rightarrow (CH_3C_6H_4O)_n$ | Oxidation of cresol and detection of formed polymer |
| Crotonaldehyde | $CH_3CH=CHCHO + Cr^{6+} + H_2SO_4 \rightarrow Cr^{3+}$ | Detection of reduced Chromium Oxide |
| Methyl Ethyl Ketone | $CH_3COC_2H_5 + Cr^{6+} + H_2SO_4 \rightarrow Cr^{3+}$ | Detection of reduced Dichromate |
| Propylene Glycol | $CH_3CH(OH)CH_2OH + 2 HIO_4 \rightarrow 3 HCHO + 2 HIO_3 + H_2O$ $HCHO + HIO_4 + H_2SO_4 \rightarrow HCOOH + HIO_3$ $HCOOH + NaOH \rightarrow Na(HCOO) + H_2O$ | Detection of formic acid by pH indicator |
| Furfural | $CH_2=CHO + Cr^{6+} + H_2SO_4 \rightarrow Cr^{3+} + CH=C-CHO$ | Detection of reduced chromium oxide |

The amount of target compound present in a vapor sample (e.g., one or more puffs) of an aerosol varies and generally depends on the amount of the corresponding impurity present in the aerosol precursor from which the target compound was formed during vaporization. In some embodiments, the target compound present in the aerosol ranges from 0.01 ppm to about 1000 ppm. Because the amount of target compound to be detected various the amount of colorimetric indicator material can vary as well.

For methods directed towards detecting the presence or absence of a predetermined amount target compound present in a certain volume (i.e., number of puffs) of aerosol a colorimetric indicator material is used in a predetermined amount. As the colorimetric indicator material is exposed to the aerosol passing through the colorimetric aerosol detection device as discussed above, the colorimetric indicator material undergoes a change in color from one color to a different color when a predetermined amount of the target compound is detected.

For a method of quantifying an amount of a target compound present in a certain volume of aerosol, a fixed amount of indicator material is located inside the tubular housing of the colorimetric aerosol detection device forming a bed that corresponds with the concentration scale provided on the outside of the tubular housing. As the aerosol passes through the bed of colorimetric indicator material, the colorimetric indicator material undergoes a color-changing reaction when detecting the target compound. The amount of target compound being detected is visualized by the length of the discolored band of the bed of the colorimetric indicator material having undergone a color-change, which corresponds to the concentration scale provided on the outside of the tubular housing. The consumer can visually read off the concentration provided by the concentration scale in ppm units and can determine the amount of target compound present in a given sample volume of the aerosol.

In some embodiments, a product insert accompanies the colorimetric aerosol detection device containing health safety information related to the target compound or class of target compounds to be detected with the colorimetric aerosol detection device. The health safety information includes, but is not limited to, allowable acute exposure limits and/or ranges of exposure limits via inhalation of the target compound or class of target compounds as determined by public and government health agencies such as the Occupational Safety and Health Administration (OSHA), Environmental Protection Agency (EPA), National Institute of Occupational Safety and Health (NIOSH), World Health Organization (WHO), and others.

For colorimetric aerosol detection devices designed to detect the presence or absence of a target compound in an aerosol, the amount of colorimetric indicator material typically employed corresponds to detecting an amount of the target compound exceeding an allowable amount according to the above mentioned health agencies. A color change of the indicator material in such a detection device indicates to the consumer that the target compound is present in the aerosol in an exceeding amount and may present a health hazard when consumed.

For colorimetric aerosol detection devices designed to measure the concentration of a target compound as mentioned above, the consumer would be able to compare the measured value obtained from the colorimetric aerosol detection device with the allowable acute exposure limit of the target compound provided in the product insert to determine whether the measured value is allowable.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

EXAMPLE

Aspects of the present invention are more fully illustrated by the following example, which is set forth to illustrate certain aspects of the present invention and is not to be construed as limiting thereof.

An ASPIRE e-cigarette vapor device was filled with approximately 2 mL of a commercially available e-liquid. The aerosol sample collection was conducted from a Cerulean SM 450 Linear Smoke Machine using a square wave profile. The target aerosolizing regimen was 55 mL puff volume, 3 second puff duration, and 30 second puff interval. Three puffs were collected in a formaldehyde colorimetric detection tube manufactured from Sensidyne Industrial Health and Safety Instrumentation. The power units were fully charged prior to testing. The room conditions were maintained at 60%+/−2% relative humidity, 22° C.+/−2.0° C., and barometric pressure 715-745 mm/Hg. Millex PTFE vacuum line Protector (filter) was placed behind the Sensidyne indicator tube in order to protect the puff engines inside the Cerulean SM450 Linear Smoke Machine. After 3 puffs color change, indicating the presence of formaldehyde was observed in the tube. Approximately 0.3 ppm of formaldehyde was detected. The detection tube and its components were disposed since this is a one-time use device. This example illustrated that a colorimetric device can be used to detect target compounds for an e-cigarette device.

That which is claimed:

1. A colorimetric aerosol detection device adapted for engagement with an aerosol delivery device having a mouthpiece, comprising:
   a tubular housing having a first open end and a second open end such that a stream of vapor can pass through the tubular housing in a direction from the first open end to the second open end, wherein the first open end is configured to engage the mouthpiece of the aerosol delivery device such that vapor produced in the aerosol delivery device is in fluid communication with the first open end, and the second open end is configured as a mouthpiece through which a user can draw the stream of vapor into the tubular housing by suction, and wherein at least a portion of the tubular housing is transparent or translucent; and
   a colorimetric indicator material disposed inside the tubular housing between the first end and the second end, wherein the colorimetric indicator material is configured to signal detection of a target compound in the stream of vapor passing through the tubular housing by a change in color visible to the user through the transparent or translucent portion of the tubular housing.

2. The colorimetric aerosol detection device of claim 1, wherein the tubular housing is made of polypropylene, polycarbonate, glass, stainless steel, or combinations thereof.

3. The colorimetric aerosol detection device of claim 1, wherein the transparent or translucent portion of the tubular housing has a length that is at least 50% of the longitudinal length of the tubular housing showing the colorimetric indicator material disposed inside the housing.

4. The colorimetric aerosol detection device of claim 1, wherein the transparent or translucent portion of the tubular housing has a concentration scale.

5. The colorimetric aerosol detection device of claim 1, wherein the aerosol delivery device is an electronic cigarette.

6. The colorimetric aerosol detection device of claim 1, further comprising a sealing element located at the first end inside the tubular housing upstream of the colorimetric indicator material.

7. The colorimetric aerosol detection device of claim 6, wherein the sealing element is made of silicon or rubber.

8. The colorimetric aerosol detection device of claim 7, wherein the sealing element is a gasket.

9. The colorimetric aerosol detection device of claim 6, wherein the sealing element is configured to form a tight seal between the aerosol detection device and an aerosol delivery device attached thereto to prevent portions of the stream of vapor produced from the aerosol delivery device to escape from the colorimetric aerosol device into the atmosphere.

10. The colorimetric aerosol detection device of claim 1, wherein the colorimetric indicator material is organic, inorganic, organometallic, transition metal complexes or a combination thereof.

11. The colorimetric aerosol detection device of claim 1, wherein the colorimetric indicator material is present in an amount to detect a predetermined amount of a target compound.

12. The colorimetric aerosol detection device of claim 1, wherein the colorimetric indicator material detects a target compound comprising an electrophilic, nucleophilic, or metal-containing functional group.

13. The colorimetric aerosol detection device of claim 1, wherein the colorimetric indicator material is disposed on a porous support material.

14. The colorimetric aerosol detection device of claim 13, wherein the porous support material is selected from the group consisting of porous particles, particle beads, fibrous materials and combinations thereof.

15. The colorimetric aerosol detection device of claim 14, wherein the porous support material is selected from molecular sieves, silica gels, clays, glass beads, silica glass beads, silica sands, glass fibers, plastic fibers, polymer fibers, cellulose fibers, papers, membranes, organic cottons, wools, regenerated celluloses, and combinations thereof.

16. The colorimetric aerosol detection device of claim 1, wherein the colorimetric indicator material inside the tubular housing occupies at least about 50% of the total inside volume of the tubular housing.

17. The colorimetric aerosol detection device of claim 1, further comprising an adsorbent material disposed inside the tubular housing located downstream of the chemical indicator material.

18. The colorimetric aerosol detection device of claim 17, wherein the adsorbent material is selected from activated carbon, molecular sieves, clays, activated aluminas, silica gels, ion exchange resins, polyester resins, polymers, and glass fibers.

19. The colorimetric aerosol detection device of claim 17, wherein the adsorbent material inside the tubular housing occupies no more than about 50% of the total inside volume of the tubular housing.

20. A method for detecting a target compound in a stream of vapor, the method comprising:

configuring a colorimetric aerosol detection device according to claim 1 to an aerosol device such that aerosol formed in the aerosol device is passed through the colorimetric aerosol detection device as a stream of vapor and one or more target compounds in the stream of vapor is detected by the colorimetric aerosol detection device.

21. The method of claim 20, wherein the aerosol device is attached to the first open end of the tubular housing of the colorimetric aerosol detection device and a mouthpiece is attached to the second open end of the tubular housing of the colorimetric aerosol detection device.

22. The method of claim 21, wherein the aerosol is forced through the colorimetric aerosol detection device by the consumer drawing on the mouthpiece.

23. The method of claim 22, wherein the amount of aerosol passing though the colorimetric aerosol detection device is about 2 to about 4 puffs.

24. The method of claim 20, wherein the aerosol passing through the colorimetric aerosol detection device is in an amount ranging from about 100 to about 200 mL volume.

25. The method of claim 20, wherein the indicator material undergoes a change in color from one color to a different color when a predetermined amount of the one or more target compounds is detected.

26. The method of claim 20, wherein the one or more target compounds comprises an electrophilic functional group or a nucleophilic functional group.

27. The method of claim 26, wherein the electrophilic functional group comprises a carbonyl group or olefin group.

28. The method of claim 27, wherein the one or more target compounds comprise 1,3-butadiene, formaldehyde, acetaldehyde, acrolein, crotonaldehyde, methyl ethyl ketone, furfural, diacetyl, acetone, 2,3-pentanedione, or combinations thereof.

29. The method of claim 26, wherein the nucleophilic functional group comprises a carboxyl group or a hydroxy group.

30. The method of claim 29, wherein the one or more target compounds comprise butyric acid, cresol, propylene glycol, or combinations thereof.

* * * * *